United States Patent [19]
Kristiansen et al.

[11] Patent Number: 5,952,363
[45] Date of Patent: Sep. 14, 1999

[54] PYRROLIDINE COMPOUNDS USEFUL IN THE TREATMENT OF DIABETES

[75] Inventors: Marit Kristiansen, Søborg; Palle Jakobsen, Værløse; Jane Marie Lundbeck, Glostrup, all of Denmark

[73] Assignee: Novo Nordisk A/S, Bagsvaerd, Denmark

[21] Appl. No.: 09/035,494

[22] Filed: Mar. 5, 1998

Related U.S. Application Data

[60] Provisional application No. 60/042,632, Apr. 4, 1997.

[30] Foreign Application Priority Data

Mar. 4, 1997 [DK] Denmark ................................ 0248/97

[51] Int. Cl.$^6$ ..................... A61K 31/40; C07D 207/09; C07D 207/12; C07D 207/14
[52] U.S. Cl. ..................... 514/408; 514/424; 514/425; 514/426; 514/428; 548/541; 548/543; 548/556; 548/557; 548/566; 548/570
[58] Field of Search ..................... 514/408, 424, 514/425, 426, 428; 548/556, 557, 566, 570, 541, 543

[56] References Cited

U.S. PATENT DOCUMENTS 4,996,329  2/1991  Fleet et al. ................ 548/453

FOREIGN PATENT DOCUMENTS

WO 97/09040  3/1997  WIPO .

OTHER PUBLICATIONS

Fairbanks et al., Tetrahedron, vol. 48, No. 16, pp. 3365–3376 (1992).
Brandstetter et al., Tetrahedron Letter, vol. 36, No. 41, pp. 7511–7514, (1995).
Winchester et al., Biochem J., vol. 290, pp. 743–749 (1993).
Kimura et al., *Journal of Traditional Medicines*, vol. 12, pp. 214–219 (1995).
Fairbanks et al., "Synthesis of, and Lack of Inhibition of a Rhamnosidase by, Both Enantiomers of Deoxyrhamnojirimycin and Rhamnonolactam: Beta–Mannosidase Inhibition by Gamma–lactams," Tetrahedron, vol. 48, No. 16, pp. 3365–3376, Apr. 17, 1992.

*Primary Examiner*—Johann Richter
*Assistant Examiner*—Jane C. Osewcki
*Attorney, Agent, or Firm*—Steve T. Zelson; Valeta A. Gregg; Carol E. Rozek

[57] ABSTRACT

The present invention relates to novel pyrrolidine compounds having the general formula I

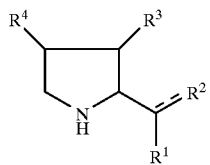

(I)

and pharmaceutically acceptable acid addition salts or hydrates or prodrugs thereof, wherein $R^1$ is straight or branched $C_{1-14}$-alkyl optionally substituted with $C_{3-7}$-cycloalkyl, $C_{1-6}$-alkoxy, phenoxy, perhalomethyl, halogen, optionally substituted phenyl;

$C\!\!=\!\!\!=\!\!R^2$ is optionally $C\!\!=\!\!R^2$ or $C\!\!-\!\!R^2$ $R^2$ is oxygen, hydroxy, halogen, amino or mercapto, $R^3$ and $R^4$ independently are hydroxy, halogen, amino or mercapto, the use of these compounds as medicament, the use of these medicaments in the treatment of diabetes, pharmaceutical compositions containing these compounds and methods of preparing the compounds.

11 Claims, No Drawings

PYRROLIDINE COMPOUNDS USEFUL IN THE TREATMENT OF DIABETES

CROSS-REFERENCE TO RELATED APPLICATIONS

This application claims priority under 35 U.S.C. 119 of Danish application 0248/97 filed on Mar. 7, 1997 and U.S. provisional serial No. 60/042,632 filed on Apr. 4, 1997, the contents of the latter of which which is fully incorporated herein by reference.

The present invention relates to novel compounds, the use of these compounds as medicaments, the use of these medicaments in the treatment and/or prevention of diabetes, and especially non-insulin dependent diabetes (NIDDM or type 2 diabetes) including overnight or meal treatment and treatment or prevention of long-term complications, such as retinopathy, neuropathy, nephropathy, and micro- and macroangiopathy; treatment of hyperglycemia, hypercholesterolemia, hypertension, hyperinsulinemia, hyperlipidemia, atherosclerosis, or myocardial ischemia; pharmaceutical compositions containing these compounds, and methods of preparing the compounds.

Diabetes is characterized by an impaired glucose metabolism manifesting itself among other things by an elevated blood glucose level in the diabetic patients. Underlying defects lead to a classification of diabetes into two major groups: type 1 diabetes, or insulin demanding diabetes mellitus (IDDM), which arises when patients lack β-cells producing insulin in their pancreatic glands, and type 2 diabetes or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulfonylureas that stimulate β-cell function or with agents that enhance the tissue sensitivity of the patients towards insulin or with insulin. Among the agents applied to enhance tissue sensitivity towards insulin metformin is a representative example. Even though sulfonylureas are widely used in the treatment of NIDDM this therapy is, in most instances, not satisfactory: In a large number of NIDDM patients sulfonylureas do not suffice to normalize blood sugar levels and the patients are, therefore, at high risk for acquiring diabetic complications. Also, many patients gradually lose the ability to respond to treatment with sulfonylureas and are thus gradually forced into insulin treatment. This shift of patients from oral hypoglycaemic agents to insulin therapy is usually ascribed to exhaustion of the β-cells in NIDDM patients.

In normals as well as in diabetics, the liver produces glucose in order to avoid hypoglycaemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production (reviewed in R. A. De Fronzo: *Diabetes* 37 (1988), 667–687; A. Consoli: *Diabetes Care* 15 (1992), 430–441; and J. E. Gerich: *Horm.Metab.Res.* 26 (1992), 18–21). Similarly, hepatic glucose production will be increased in type 1 diabetes, if the disease is not properly controlled by insulin treatment. Since existing forms of therapy of diabetes does not lead to sufficient glycaemic control and therefore are unsatisfactory, there is a great demand for novel therapeutic approaches. Since the liver in diabetes is known to have an increased glucose production, compounds inhibiting this activity are highly desirable. Recently, patent applications on inhibitors of the liver specific enzyme, glucose-6-phosphatase, which is necessary for the release of glucose from the liver, have been filed, for example German Offenlegunqsschrift Nos. 4,202,183 and 4,202,184 and Japanese patent application No. 4-58565. All these known compounds are benzene derivatives. Substituted N-(indole-2-carbonyl)-glycinamides acting as glycogen phosporylase inhibitors are disclosed in PCT-publications No. WO96/39384 and WO96/39385.

Atherosclerosis, a disease of the arteries, is recognized to be the leading cause of death in the United Stated and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in color due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extra cellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Such independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition which occurs in the human population as a secondary symptom to various other disorders such as renal artery stenosis, pheochromocytoma or endocrine disorders. However, hypertension is also evidenced in many patients in whom the causative agent or disorder is unknown. While such "essential" hypertension is often associated with disorders such as obesity, diabetes and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure and stroke (brain hemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin, aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus, a broad range of beta-blockers, vasoconstrictors, angiotensin converting enzyme inhibitors and the like have been developed and marketed as antihypertensives. The treatment of hypertension utilizing these compounds have proven beneficial in the prevention of short-interval deaths such as heart failure, renal failure and brain hemorrhaging. However, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention among other things. These latter functions can be accomplished without affecting glucose levels and are known causes of hypertension. Peripheral vasculature growth, for example, can cause constriction of peripheral capillaries; while sodium retention increases blood volume. Thus, the lowering of insulin levels in hyperinsulinemics can prevent abnormal vascular growth and renal sodium retention caused by high insulin levels and thereby alleviate hypertension.

Cardiac hypertrophy is a significant risk factor in the development of sudden death, myocardial infarction, and congestive heart failure. These cardiac events are due, at least in part, to increased susceptibility to myocardial injury after ischemia and reperfusion which can occur in outpatient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20–25% in some series. In addition, of the 400,000 patients undergoing coronary by-pass surgery annually, perioperative myocardial infarction is estimated to occur in 5% and death in 1–2%. There is currently no drug therapy in this area which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

One object of the present invention is to provide compounds which can be used as medicaments for treating one or more of the above-mentioned diseases and disorders.

A further object of this invention is to provide compounds which can effectively be used in the treatment of diabetes, preferably type II diabetes, including overnight or meal treatment, and preferably for the treatment of increased plasma glucose levels.

Besides, it is an object of the invention to provide compounds having a reduced risk of side effects, and which can effectively be used as medicaments for long-term treatment.

A still further object of this invention is to provide compounds which can effectively be used as inhibitors of glucose production from the liver.

A still further object of this invention is to provide further compounds which can be effectively used as phosphorylase inhibitors, preferably as glycogen phosphorylase inhibitors.

It has now been found that members of a novel group of pyrrolidine compounds have interesting pharmacological properties. For example, the compounds of this invention can be used in the treatment of diabetes. Especially, the compounds of this invention are active as inhibitors of glucose production from the liver. Consequently, the compounds of this invention can be used for the treatment of the increased plasma glucose levels in diabetics.

Accordingly, it is an object of the invention to provide such novel pyrrolidine compounds.

DETAILED DESCRIPTION OF THE INVENTION

The compounds of the invention are compounds of the general formula I

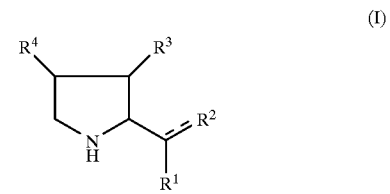

and pharmaceutically acceptable acid addition salts or hydrates or prodrugs hereof, wherein $R^1$ is straight or branched $C_{1-14}$-alkyl optionally substituted with $C_{3-7}$-cycloalkyl, $C_{1-6}$-alkoxy, phenoxy, perhalomethyl, halogen, optionally substituted phenyl;

$C\text{---}R^2$ is optionally $C{=}R^2$ or $C{-}R^2$ $R^2$ is oxygen, hydroxy, halogen, amino or mercapto, $R^3$ and $R^4$ independently are hydroxy, halogen, amino or mercapto.

The compounds of formula I may be presented as a mixture of enantiomers which, if desired, may be resolved into the individual pure enantiomers. This resolution may conveniently be performed by fractional crystallization from various solvents, of the salts of compounds of the formula I with optical active acids or by other methods known per se, for example, chiral column chromatography. This invention includes all isomers, whether resolved or mixtures thereof.

Examples of pharmaceutically acceptable salts are acid addition salts with non-toxic acids, either inorganic acids such as hydrochloric acid, hydrobromic acid, hydroiodic acid, sulphuric acid and phosphoric acid, or organic acids such as formic acid, acetic acid, trifluoroacetic acid, trichloroacetic acid, propinoic acid, succinic acid, gluconic acid, lactic acid, citric acid, ascorbic acid, benzoic acid, embonic acid, methanesulphonic and ethanesulfonic acid, malonic acid, oxalic acid, maleic acid, pyruvic acid, tartaric acid, fumaric acid, mandelic acid, cinnamic acid, picric acid and the like acids, and include the pharmaceutically acceptable salts listed in Journal of Pharmaceutical Science, 66, 2 (1977) and incorporated herein by reference; pharmaceutically acceptable metal salts, such as lithium, sodium, potassium, or magnesium salts and the like. Also intended as pharmaceutically acceptable acid addition salts are the hydrates which the present compounds are able to form. The acid addition salts may be obtained as the direct products of compound synthesis. In the alternative, the free base may be dissolved in a suitable solvent containing the appropriate acid, and the salt isolated by evaporating the solvent or otherwise separating the salt and solvent. The compounds of this invention may form solvates with standard low molecular weight solvents using methods known to the skilled artisan.

In the above structural formula and throughout the present specification, the following terms have the indicated meaning:

The term "$C_{1-6}$-alkoxy" as used herein, alone or in combination, is intended to include those $C_{1-6}$ alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy, and hexoxy. Examples of branched alkoxy groups are isopropoxy, sec-butoxy, tert-butoxy, isopentoxy, and isohexoxy. Examples of cyclic alkoxy groups are cyclopropyloxy, cyclobutyloxy, cyclopentyloxy, and cyclohexyloxy.

The term "$C_{3-7}$-cycloalkyl" as used herein refers to a radical of a saturated cyclic hydrocarbon with the indicated number of carbons such as cyclopropyl, cyclobutyl, cyclopentyl, cyclohexyl or cycloheptyl.

The term "halogen" means fluorine, chlorine, bromine or iodine.

The term "perhalomethyl" means trifluoromethyl, trichloromethyl, tribromomethyl or triiodomethyl.

The term "$C_{1-14}$-alkyl" as used herein, alone or in combination, refers to a straight or branched, saturated hydrocarbon chain having the indicated number of carbon atoms. Typical $C_{1-14}$ alkyl groups include, but are not limited to methyl, ethyl, n-propyl, isopropyl, n-butyl, sec-butyl, isobutyl, tert-butyl, n-pentyl, 2-methylbutyl, 3-methylbutyl, 4-methylpentyl, neopentyl, n-hexyl, 1,2-dimethylpropyl, 2,2-dimethylpropyl, 1,2,2-trimethylpropyl, tridecyl and the like. The term "$C_{1-14}$-alkyl" as used herein also includes secondary $C_{3-6}$-alkyl and tertiary $C_{4-6}$-alkyl.

The term "prodrug" as used herein refers to e.g. to compounds of formula I in which an ester group has been introduced.

Certain of the above defined terms may occur more than once in the above formula 1, and upon such occurrence each term shall be defined independently of the other.

The compounds of the invention may have one or more asymmetric centres and it is intended that stereoisomers (optical isomers), as separated, pure, or partially purified stereoisomers or racemic mixtures thereof are included in the scope of the invention.

In a preferred embodiment $C=\!=\!=\!R^2$ is C—R2 wherein R2 has the meaning defined above, and preferably is hydroxy.

In another preferred embodiment R3 and R4 are both hydroxy.

Preferred compounds of the invention are:
(3R,4R)-2-(1-hydroxyethyl)-3,4-pyrrolidinediol,
(3R,4R)-2-(1-hydroxypropyl)-3,4-pyrrolidinediol,
(3R,4R)-2-(1-hydroxypentyl)-3,4-pyrrolidinediol,
(3R,4R)-2-(1-hydroxytridecyl)-3,4-pyrrolidinediol,
(3R,4R)-2-(1-hydroxyphenylbutyl)-3,4-pyrrolidinediol, and
(3R,4R)-2-(1-hydroxyethyl)-3,4-pyrrolidinediol.
or pharmaceutically acceptable salts or hydrates thereof as defined herein, or any optical isomer or mixture of optical isomers, including a racemic mixture, or any tautomeric form.

The present invention also relates to an optical isomer or mixture of optical isomers, including a racemic mixture of compounds of formula I selected from the group consisting of:
(2R,3R,4R)-2-acetyl-3,4-pyrrolidinediol,
(2R,3R,4R)-2-(1-hydroxyethyl)-3,4-pyrrolidinediol,
(2R,3R,4R)-2-(1-hydroxypropyl)-3,4-pyrrolidinediol,
(2R,3R,4R)-2-(1-hydroxypentyl)-3,4-pyrrolidinediol,
(2R,3R,4R)-2-(1-hydroxytridecyl)-3,4-pyrrolidinediol,
(2S,3S,4S)-2-acetyl-3,4-pyrrolidinediol,
(2S,3S,4S)-2-(1-hydroxyethyl)-3,4-pyrrolidinediol,
(2S,3S,4S)-2-(1-hydroxypropyl)-3,4-pyrrolidinediol,
(2S,3S,4S)-2-(1-hydroxypentyl)-3,4-pyrrolidinediol,
(2S,3S,4S)-2-(1-hydroxytridecyl)-3,4-pyrrolidinediol,
(2R,3R,4R)-2-((1R)-1-hydroxyethyl)-3,4-pyrrolidinediol,
(2R,3R,4R)-2-((1R)-1-hydroxypropyl)-3,4-pyrrolidinediol,
(2R,3R,4R)-2-((1R)-1-hydroxypentyl)-3,4-pyrrolidinediol,
(2R,3R,4R)-2-((1R)-1-hydroxytridecyl)-3,4-pyrrolidinediol,
(2S,3S,4S)-2-((1R)-1-hydroxyethyl)-3,4-pyrrolidinediol,
(2S,3S,4S)-2-((1R)-1-hydroxypropyl)-3,4-pyrrolidinediol,
(2S,3S,4S)-2-((1R)-1-hydroxypentyl)-3,4-pyrrolidinediol,
(2S,3S,4S)-2-((1R)-1-hydroxytridecyl)-3,4-pyrrolidinediol,
(2R,3R,4R)-2-((1S)-1-hydroxyethyl)-3,4-pyrrolidinediol,
(2R,3R,4R)-2-((1S)-1-hydroxypropyl)-3,4-pyrrolidinediol,
(2R,3R,4R)-2-((1S)-1-hydroxypentyl)-3,4-pyrrolidinediol,
(2R,3R,4R)-2-((1S)-1-hydroxytridecyl)-3,4-pyrrolidinediol,
(2S,3S,4S)-2-((1S)-1-hydroxyethyl)-3,4-pyrrolidinediol,
(2S,3S,4S)-2-((1S)-1-hydroxypropyl)-3,4-pyrrolidinediol,
(2S,3S,4S)-2-((1S)-1-hydroxypentyl)-3,4-pyrrolidinediol, and
(2S,3S,4S)-2-((1S)-1-hydroxytridecyl)-3,4-pyrrolidinediol,
or a pharmaceutically acceptable addition salts or hydrates thereof.

The present invention also relates to the use of the novel compounds of the formula I as disclosed in the examples herein, and as defined in the compound claims herein, for the preparation of a medicament, especially for the preparation of a medicament for the treatment and/or prevention of hyperglycaemia or diabetes mellitus, preferably NIDDM. The compounds of the present invention reduce elevated plasma glucose levels, and hence make them useful in the treatment and prevention of various diseases of the endocrinological system, especially ailments related to carbohydrate metabolism and especially the glucose metabolism, e.g. hyperglycaemia, diabetes mellitus, and especially non-insulin dependent diabetes mellitus (NIDDM) including long-term complications, such as retinopathy, neuropathy, nephropathy, and micro- and macroangiopathy. Moreover, the present compounds are useful in the prophylactic treatment of hyperlipidaemia, hypertension, liver and bile diseases, and atherosclerosis associated with diabetes. The present compounds are especially useful in the treatment of diseases associated with the activity of the liver enzyme glycogen phosphorylase, due to their capability of inhibiting said enzymatic activity.

Accordingly, in another aspect the invention relates to a compound of the general formula I, or a pharmaceutically acceptable acid addition salts or hydrates or prodrugs thereof for use as a therapeutically active substance, preferably for use as a therapeutically active substance in the treatment or prevention of diseases of the endocrinological system, preferably hyperglycaemia or diabetes.

Furthermore, the invention also relates to the use of the inventive compounds of formula I for the preparation of medicaments useful for treating or preventing hyperglycaemia or diabetes. Moreover, the invention relates to a method of treating or preventing diseases of the endocrinological system, preferably diabetes, in a subject in need thereof comprising administering an effective amount of a compound according to the invention.

The invention also relates to methods of preparing the above mentioned compounds. These methods comprise:

a) Reacting a compound of formula II (II)

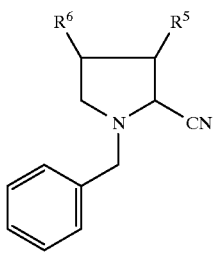

wherein $R^5$ is $R^3$ optionally substituted with a protection group, preferably benzyl, $R^6$ is $R^4$ optionally substituted with a protection group, preferably benzyl and $R^3$ and $R^4$ are as defined above with $R^1$ MgX wherein $R^1$ is as defined above and X is halogen, preferably bromine or chlorine, to form a compound of formula III (III)

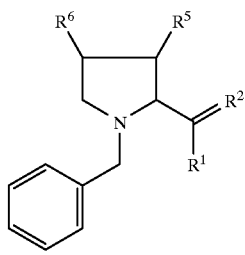

wherein $R^2$ is oxygen and $R^1$, $R^5$ and $R^6$ have the meanings set forth above, followed by debenzylation and optionally deprotection of a compound of formula (III) by catalytic reduction to form a compound of the general formula (I), or b) Reduction of a compound of formula III (III)

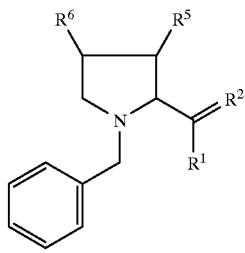

with a reducing agent, preferably LiAlH$_4$ in THF to form a compound of formula IV (IV)

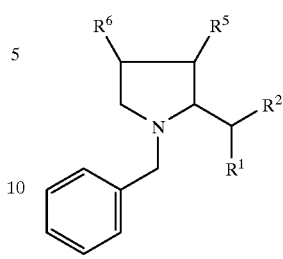

wherein $R^2$ is hydroxy and $R^1$, $R^5$ and $R^6$ have the meanings set forth above, followed by debenzylation and optionally deprotection of a compound of formula (IV) by catalytic reduction to form a compound of the general formula (I).

The starting materials employed in the synthesis of the compounds of formula I are either known or may be prepared in conventional manner from commercially available materials, e.g according to the methods described in the examples. Other compounds of the general formula I can be prepared by the above strategy. A variety of functional groups can be introduced in the compounds prepared as outlined above by methods well known to those skilled in the art.

Pharmaceutical Compositions

This invention further provides pharmaceutical compositions comprising, as an active ingredient, at least one compound of formula I or a pharmaceutically acceptable salt thereof in connection with a pharmaceutically acceptable carrier or diluent. Such compositions may be in the form of powders, solutions, suspensions, or aerosols, or which may or may not be divided in unit dosage form or in the form of capsules or tablets. Liquid compositions include sterile solutions, suspensions and emulsions suitable for parenteral injection.

The pharmaceutical compositions of this invention may comprise carriers, diluents, absorption enhancers, tablet disintegrating agents and other ingredients which are conventionally used in the art. The powders and tablets preferably contain from 5 to 99%, more preferred from 10 to 90% of the active ingredient. Examples of solid carriers are magnesium carbonate, magnesium stearate, dextrin, lactose, sugar, talc, gelatine, pectin, tragacanth, methyl cellulose, sodium carboxymethyl cellulose, low melting waxes and cocoa butter.

The route of administration of the compositions containing a compound of formula I may be any route which effectively transports the active compound to its site of action, such as oral, pulmonary, transdermal or parenteral e.g. rectal, depot, subcutaneous, intravenous, intraurethral or intramuscular, the oral route being preferred.

If a solid carrier is used for oral administration the preparation may be tabletted, placed in a hard gelatin capsule in powder or pellet form, or it can be in the form of a troche or lozenge. If a liquid carrier is used the preparation may be in the form of a syrup, emulsion, soft gelatin capsule or sterile injectable liquid such as an aqueous or nonaqueous liquid suspension or solution. Tablets, dragees, or capsules having talc and/or a carbohydrate carrier or binder or the like are particularly suitable for oral application. Preferable carriers for tablets, dragees, and capsules include lactose, corn starch, and/or potato starch.

For parenteral application particularly suitable are injectable solutions or suspensions, preferably aqueous solutons with the active compound dissolved in polyhydroxylated castor oil.

A typical tablet which may be prepared by conventional tabletting techniques may contain:

Core:
- Active compound (as free compound or salt thereof) 50 mg
- Colloidal silicon dioxide (Aerosil) 1.5 mg
- Cellulose, microcryst. (Avicel) 70 mg
- Modified cellulose gum (Ac-Di-Sol) 7.5 mg
- Magnesium stearate Ad.

Coating:
- HPMC approx. 9 mg
- *Mywacett 9–40 T approx. 0.9 mg
- *Acylated monoglyceride used as plasticizer for film coating.

The compounds of the invention may be administered to a mammal, especially a human in need of such treatment, prevention, elimination, alleviation or amelioration of the various diseases as mentioned above and especially diabetes. Such mammals include also animals, both domestic animals, e.g. household pets, and non-domestic animals such as wildlife.

The regimen for any patient to be treated with the compositions according to the present invention should be determined by those skilled in the art. The daily dose to be administered in therapy can be determined by a physician and will depend on the particular compound employed, on the route of administration and on the age and the condition of the patient.

The compounds of the invention are effective over a wide dosage range. For example, in the treatment of adult humans, dosages from about 2 to about 500 mg per day may be used. The exact dosage will depend upon the mode of administration, on the therapy desired, form in which administered, the subject to be treated and the body weight of the subject to be treated, and the preference and experience of the physician or veterinarian in charge.

In a further aspect, the present invention relates to a method of treating and/or preventing diabetes.

In a still further aspect, the present invention relates to the use of one or more compounds of the general formula I or pharmaceutically acceptable salts thereof for the preparation of a medicament for the treatment and/or prevention of diabetes.

Experimental pharmacological protocol and results

For in vivo studies, female ob/OB mice (20 g) fasted for 3 hours were used. Test compounds or NaCl (0.9%; controls) were administered intraveneously (hereinafter designated i.v.). Glucagon were administered subcutaneously (hereinafter designated s.c.) in order to increase hepatic glucose output derived from glycogen. Blood samples were drawn from the orbital vain and analyzed for glucose using a glucose oxidase method.

Rat hepatocytes were isolated using a standard two step collagenase technique, and cultured onto collagen coated culture dishes for 72 hours in medium 199 with the addition of dexamethazone (0.1 mM); penicillin/Streptomycin ((100 u/100 mg)/ml) and insulin (1 nM). During the last 24 hours, the hepatocytes were cultured in the presence of high levels of insulin (5 nM) and glucose (15 mM), which result in the incorporation of glucose into glycogen. Therefore, at the time of the experiment, the cells mimic livers from fed animals. Experiments were initiated after 48 hours of culture by 2 times wash of cells and addition of a 20 mM HEPES experimental buffer including balanced salts, but without glucose. The test compound was added simultaneously with the experimental buffer. To some cultures, glucagon (0.5 nM) was added after 10 minutes in order to stimulate glucose production from liver cells. The glucose released into the media, reflecting the glucose production of the liver cells, was measured 70 minutes after the start of the experiment and standardized to cellular DNA content.

Phosphorylase was either purchased from Sigma or extracted from rat livers according to Stalmans et. al. (Eur.J.Biochem. 49 (1974), 415). The activity of phosphorylase was determined as described by Bergmeyer (1983; in: Meth. of Enzymatic Analysis, 2, 293–295, Weinheim, (ed.) Verlag Chemie).

Compounds of the invention shows their effect in lowering the glucagon mediated increase in plasma glucose.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLE 1

(3S,4S)-1-Benzyl-3,4-dihydroxy-2,5-dioxopyrrolidine

A mixture of D(-)-tartaric acid (4.5 g, 30 mmol), benzylamine (3.3 ml, 30,2 mmol) and m-xylene (50 ml) was heated at reflux temperature for 4 hours with simultaneous capture of water. The mixture was cooled to room temperature, filtered and washed with m-xylene twice (2×2 ml) and acetone (10 ml) to give (3S,4S)-1-benzyl-3,4-dihydroxy-2,5-dioxopyrrolidine (5.0 g, yield: 76%) as light yellow crystals.

MP. 195–97° C.

EXAMPLE 2

(3R,4R)-1-Benzyl-3,4-pyrrolidinediol

Boron trifluoride ethyl etherate (36 ml, 0.29 mol) in diglyme (150 ml) was cooled to 0+ C. (3S,4S)-1-Benzyl-3,4-dihydroxy-2,5-dioxopyrrolidine (16 g, 72 mmol) and sodium borohydride were added slowly. The mixture was stirred at 70° C. for 2 hours. 6 N hydrochloric acid (100 ml) was added slowly and the mixture was heated at 70° C. for 15 minutes. Sodium fluoride (44.5 g, 1 mol) was added and the mixture was heated at reflux temperature for ½ hour. The mixture was cooled to room temperature. 20% Aqueous sodium hydroxide (85 ml) was added and the resulting mixture was filtered. The organic phase was isolated and evaporated to dryness. The residue was partitioned between water and diethyl ether. The water phase was extracted with ether (4×500 ml). The collected organic phases were dried over magnesium sulphate and evaporated to dryness. Recrystallization from ethyl acetate (25 ml) gave (3R,4R)-1-benzyl-3,4-pyrrolidinediol (12.3 g, yield: 88%) as white crystals.

Mp. 97–99.7° C.

EXAMPLE 3

(3R,4R)-1-Benzyl-3,4-dibenzyloxypyrrolidine

A solution of (3R,4R)-1-benzyl-3,4-pyrrolidinediol (10 g, 51.8 mmol) in dry DMF (40 ml) was added to a suspension of 60% sodium hydride (5 g, 125 mmol) in dry DMF (150 ml) under nitrogen air. Benzyl chloride (14 ml, 120 mmol) was added and the mixture was stirred over night at room temperature.

Water was added (10 ml) and the mixture evaporated to dryness in vacuo. The residue was extracted with methylene chloride (200 ml) and ethyl acetate (50 ml). Purification of the product on silica gel (Eluent: Methylene chloride/ethyl acetate (4:1)) afforded (3R,4R)-1-benzyl-3,4-dibenzyloxypyrrolidine (15.4 g, yield: 80%) as an oil.

¹H-NMR(CDCl₃) in ppm: δ 7.3 (m, 15H), 4.48 (s, 4H), 4.05 (t, 2H), 3.6 (dd, 2H), 2.9 (dd, 2H), 2.6 (dd, 2H).

EXAMPLE 4
(3R,4R)-3,4-Dibenzyloxypyrrolidine

To a solution of (3R,4R)-1-benzyl-3,4-dibenzyloxypyrrolidine (26.8 g, 71.7 mmol) in methanol (600 ml) was added palladium hydroxide on activated charcoal (20% Pd, 2,7 g) and 25% ammonium hydroxide (6 ml). The mixture was hydrogenated in a Parr apparatus at 20 psi for 20 hours. The mixture was filtered and evaporated to dryness in vacuo to give (3R,4R)-3,4-dibenzyloxypyrrolidine (19.7 g, yield: 96%) as an oil.

¹H-NMR(CDCl₃) in ppm: δ 7.3 (m, 10H), 4.48 (s, 4H), 4.0 (m, 2H), 3.15 (dd, 2H), 2.92 (dd, 2H), 2.6 (s, 1H).

EXAMPLE 5
(3R,4R)-3.4-Dibenzyloxy-pyrrolidine-2-carbonitrile

N-Chlorosuccinimide (7.05 g, 52.6 mmol) was added to a solution of (3R,4R)-3,4-dibenzyloxypyrrolidine (15 g, 52.8 mmol) in diethyl ether (300 ml). The resulting mixture was stirred at room temperature for 3 hours under a nitrogen atmosphere. Addition of toluene (250 ml) and water (200 ml), washing of the organic phase with 2 M sodium thiosufate (200 ml) and water (200 ml), drying with magnesium sulphate gave a solution of (3R,4R)-3,4-dibenzyloxy-1-chloropyrrolidine in toluene. The compound is unstable and was used without further purification.

The toluene solution was added to a solution of 1,8-diazabicyclo[5.4.0]undec-7-ene (16 g, 105 mmol) in toluene (200 ml). The mixture was stirred at room temperature for 20 hours under a nitrogen atmosphere. Water (250 ml) was added, the organic phase was isolated and the water phase was extracted with toluene (100 ml). The combined organic phases were washed with water (200 ml), dried with magnesium sulphate giving a toluene solution of (3R,4R)-3,4-dibenzyloxy-1-pyrroline. The compound is unstable and was used without further purification.

To the toluene solution was added zinc iodide (0.5 g) and trimethylsilyl cyanide (20 ml, 160 mmol). The mixture was stirred at room temperature for 20 hours under a nitrogen atmosphere. Dioxan (5 ml) and water (5 ml) were added and stirring was continued for 1½ hour at room temperature. Water (150 ml) was added, the organic phase isolated and washed with water (200 ml), dried with magnesium sulphate and evaporated to dryness in vacuo to give the title compound as an oil. Purification of the crude product on a silica gel column (Eluent: ethyl acetate) afforded (3R,4R)-3,4-dibenzyloxy-pyrrolidine-2-carbonitrile (13.5 g, yield: 82% overall) as an oil.

¹H-NMR(CDCl₃) in ppm: δ 7.33 (m, 10H), 4.48–4.7 (m, 4H), 3.9–4.3 (m, 3H), 3.4–3.0 (m, 2H), 2.2 (broad s, 1H).

EXAMPLE 6
(3R,4R)-1-Benzyl-3.4-dibenzyloxy-pyrrolidine-2-carbonitrile

A mixture of (3R,4R)-3,4-dibenzyloxy-pyrrolidine-2-carbonitrile (13 g, 42.2 mmol), potassium carbonate (8.7 g, 63 mmol), potassium iodide (0.1 g), benzyl bromide (7.5 ml, 63.2 mmol) and acetone (200 ml) were heated at reflux temperature for 4 hours. The mixture was cooled, filtered and the filtrate evaporated to dryness in vacuo to give the title compound as an oil. Purification of the crude product on a silica gel column (Eluent: From 100% heptane to 100% ethyl acetate) afforded (3R,4R)-1-benzyl-3,4-dibenzyloxy-pyrrolidine-2-carbonitrile (8.2 g, yield: 49%) as an oil.

¹H-NMR(CDCl₃) in ppm: δ 7.28 (m, 15H), 4.4–4.6 (m, 4H), 3.55–4.3 (m, 5H), 3.2–2.6 (m, 2H).

The oil of 1-benzyl-3,4-dibenzyloxy-pyrrolidine-2-carbonitrile contains a mixture of two stereoisomers. A small amount of the two isomers were isolated on a reverse phase Cl 8 column (Eluent: Acetonitrile:water (7:1)+0.1% trifluoroacetic acid) giving 540 mg of (2R,3R,4R)-1-benzyl-3,4-dibenzyloxypyrrolidine-2-carbonitrile as an light yellow oil ¹H-NMR (CDCl₃) in ppm: δ 7.3 (m,15H), 4.55 (d,2H), 4.5 (s,2H), 4.23 (t,1H), 4.1 (m,1H), 3.8 (d.d,2H), 3.5 (s,1H), 3.2–2.6 (m,2H);

and 300 mg of (2S,3R,4R)-1-benzyl-3,4-dibenzyloxypyrrolidine-2-carbonitrile as an light brown oil.

¹H-NMR (CDCl₃) in ppm: δ 7.35 (m,15H), 4.6 (d.d,2H), 4.5 (d,2H), 4.2 (m,2H), 4.0 (d,1H), 3.7 (d.d,2H), 3.5 (s,1H), 2.95 (m,2H).

EXAMPLE 7
(3R,4R)-1-Benzyl-3,4-dibenzyloxy-2-acetylpyrrolidine

3 M Methylmagnesium chloride in tetrahydrofuran (0.6 ml, 1.8 mmol) was added slowly at reflux temperature to a solution of (3R,4R)-1-benzyl-3,4-dibenzyloxy-pyrrolidine-2-carbonitril (250 mg, 0.63 mmol) in diethyl ether. The mixture was heated at reflux temperature for 1 hour, cooled to room temperature and added 0.5 N hydrochloric acid (5 ml). The organic phase was isolated, washed with water (2×5 ml), dried over magnesium sulphate and concentrated in vacuo to give the title compound as an oil(200 mg, yield: 77%). Purification of the crude product on a silica gel column (Eluent: methylene chloride) afforded (3R,4R)-1-benzyl-3,4-dibenzyloxy-2-acetylpyrrolidine as an oil.

¹H-NMR(CDCl₃) in ppm: δ 7.3 (m, 15H), 4.4–4.6 (m, 4H), 3.2–4.3 (m, 6H), 2.3–2.7 (m, 1H), 2.2 (s, 3H).

In a similar way the following compounds were prepared:
(2R,3R,4R)-1-Benzyl-3,4-dibenzyloxy-2-acetylpyrrolidine from methylmagnesium chloride and (2R,3R,4R)-1-benzyl-3,4-dibenzyloxypyrrolidine-2-carbonitrile.

¹H-NMR (CDCl₃) in ppm: δ 7.3 (m,15H), 4.4–4.7 (m,4H), 4.03 (m,1H), 3,95 (m,1H), 3.7 (d.d,2H), 3.6 (d,1H), 2.6–3.2 (m,2H), 2.2 (s,3H);

(2S,3R,4R)-1-Benzyl-3,4-dibenzyloxy-2-acetylpyrrolidine from methylmagnesium chloride and (2S,3R,4R)-1-benzyl-3,4-dibenzyloxypyrrolidine-2-carbonitrile.

¹H-NMR (CDCl₃) in ppm: δ 7.3 (m,15H), 4.4–4.7 (m,4H), 4.25 (m,1H), 4.12 (m,1H), 3.7 (d.d,2H), 3.5 (m,1H), 3.4 (m,1H), 2.4 (d.d,1H), 2.18 (s,3H);

(3R,4R)-1-Benzyl-3,4-dibenzyloxy-2-valerylpyrrolidine from butylmagnesium bromide and (3R,4R)-1-benzyl-3,4-dibenzyloxy-pyrrolidine-2-carbonitrile ¹H-NMR (CDCl₃) in ppm: δ 7.3 (m,15H), 4.3–4.7 (m,4H), 3.7–4.1 (m,3H), 3.1–3.5 (m,3H), 2.1–2.7 (m,3H), 1.1–1.6 (m,4H), 0.8–1.0 (m,3H);

(3R,4R)-1-Benzyl-3,4-dibenzyloxy-2-tridecanoylpyrrolidine from dodecylmagnesium iodide and (3R,4R)-1-benzyl-3,4-dibenzyloxy-pyrrolidine-2-carbonitrile ¹H-NMR (CDCl₃) in ppm: δ 7.3 (m,15H), 4.4–4.7 (m,4H), 3.8–4.3 (m,3H), 3.1–3.7 (m,2H), 2.3–2.7 (m,2H), 1.2–1.6 (m,22H), 0.9 (b.d,3H);

(3R,4R)-1-Benzyl-3,4-dibenzyloxy-2-(4-cyclohexylbutanoyl)pyrrolidine from 3-cyclohexylpropylmagnesium chloride and (3R,4R)-1-benzyl-3,4-dibenzyloxypyrrolidine-2-carbonitrile.

¹H-NMR (CDCl₃) in ppm: δ 7.3 (m,15H), 4.4–4.6 (m,4H), 3.1–4.1 (m,5H), 2.1–2.7 (m,3H), 1.0–1.8 (m,21H), 0.7–0.95 (m,3H);

(3R,4R)-1-Benzyl-3,4-dibenzyloxy-2-(4-phenylbutanoyl) pyrrolidine from 3-phenylpropylmagnesium bromide and (3R,4R)-1-benzyl-3,4-dibenzyloxypyrrolidine-2-carbonitrile.

¹H-NMR (CDCl₃) in ppm: δ 7.3 (m,20H), 4.3–4.7 (m,4H), 3.1–4.0 (m,6H), 2.4–2.7 (m,5H), 1.8 (p,2H);

(3R,4R)-1-Benzyl-3,4-dibenzyloxy-2-propionylpyrrolidine from ethylmagnesium bromide and (3R,4R)-1-benzyl-3,4-dibenzyloxypyrrolidine-2-carbonitrile.

¹H-NMR (CDCl₃) in ppm: δ 7.3 (m,15H), 4.4–4.7 (m,4H), 3.4–4.1 (m,4H), 3.1–3.4 (m,2H), 2.3–2.8 (m,3H), 0.9 (t,3H).

EXAMPLE 8

(3R,4R)-1-Benzyl-3,4-dibenzyloxy-2-(1-hydroxyethyl) pyrrolidine

1 M lithium aluminiumhydride in tetrahydrofuran (1.5 ml, 1.5 mmol) was added slowly to a solution of (3R,4R)-1-benzyl-3,4-dibenzyloxy-2-acetylpyrrolidine (390 mg, 0.94 mmol) in dry tetrahydrofuran (5 ml) at 0–5° C. Stirring was continued for 1½ hour at room temperature. Water (1 ml) was slowly added. The mixture was filtered and the filtrate was evaporated to dryness in vacuo to give the title compound as an oil. Purification of the crude product on a silica gel column (Eluent: methylene chloride: ethyl acetate (9:1)) afforded (3R,4R)-1-benzyl-3,4-dibenzyloxy-2-(1-hydroxyethyl)pyrrolidine (90 mg, yield 23%) as an oil.

¹H-NMR(CDCl₃) in ppm: δ 7.3 (m, 15H), 4.4–4.7 (m,4H), 3.9–4.2 (m, 4H), 3.38 (d,1H), 3.05 (d, 1H), 2.5–2.8 (m, 2H), 1.2–1.3 (m, 3H).

In a similar way the following compounds were prepared:
(2R,3R,4R)-1-Benzyl-3,4-dibenzyloxy-2-(1-hydroxyethyl)pyrrolidine from (2R,3R,4R)-1-benzyl-3,4-dibenzyloxy-2-acetylpyrrolidine.

¹H-NMR(CD₃OD) in ppm: δ 7.3 (m, 15H), 4.45–4.55 (m,4H), 3.9–4.1 (m, 4H), 3.38 (d,1H), 3.05 (d, 1H), 2.5–2.6 (m, 2H), 1.18 (d, 3H).

(2S,3R,4R)-1-Benzyl-3,4-dibenzyloxy-2-(1-hydroxyethyl)pyrrolidine from (2S,3R,4R)-1-benzyl-3,4-dibenzyloxy-2-acetylpyrrolidine.

(3R,4R)-1-Benzyl-3,4-dibenzyloxy-2-(1-hydroxypentyl) pyrrolidine from (3R,4R)-1-benzyl-3,4-dibenzyloxy-2-valerylpyrrolidine;

(3R,4R)-1-Benzyl-3,4-dibenzyloxy-2-(1-hydroxytridecyl)pyrrolidine from (3R,4R)-1-benzyl-3,4-dibenzyloxy-2-tridecanoylpyrrolidine.

(3R,4R)-1-Benzyl-3,4-dibenzyloxy-2-(4-cyclohexyl-1-hydroxybutyl)pyrrolidine from (3R,4R)-1-benzyl-3,4-dibenzyloxy-2-(4-cyclohexylbutanoyl)pyrrolidine;

(3R,4R)-1-Benzyl-3,4-dibenzyloxy-2-(1-hydroxy-4-phenylbutyl)pyrrolidine from (3R,4R)-1-benzyl-3,4-dibenzyloxy-2-(4-phenylbutanoyl)pyrrolidine;

(2R,3R,4R)-1-Benzyl-3,4-dibenzyloxy-2-(1-hydroxyethyl)pyrrolidine can be separated on an optically active column into (2R,3R,4R)-1-benzyl-3,4-dibenzyloxy-2-((1R)-1-hydroxyethyl)pyrrolidine and (2R,3R,4R)-1-benzyl-3,4-dibenzyloxy-2-((1S)-1-hydroxyethyl) pyrrolidine;

(2S,3R,4R)-1-Benzyl-3,4-dibenzyloxy-2-(1-hydroxyethyl)pyrrolidine can be separated on an optically active column into (2S,3R,4R)-1-benzyl-3,4-dibenzyloxy-2-((1R)-1-hydroxyethyl)pyrrolidine and (2S,3R,4R)-1-benzyl-3,4-dibenzyloxy-2-((1S)-1-hydroxyethyl)pyrrolidine.

EXAMPLE 9

(3R,4R)-2-(1-Hydroxyethyl)-3,4-pyrrolidinediol (Compound 1)

To a solution of (3R,4R)-1-benzyl-3,4-dibenzyloxy-2-(1-hydroxyethyl)pyrrolidine (90 mg, 0.22 mmol) in abs. ethanol (10 ml) was added palladium on activated charcoal (10% Pd, 30 mg) and 37% hydrochloric acid (0.1 ml). The mixture was hydrogenated in a Parr apparatus at 40 psi for 20 hours. The mixture was filtered and evaporated to dryness in vacuo to give (3R,4R)-2-(1-hydroxyethyl)-3,4-pyrrolidinediol (36 mg, yield: 90%) as an oil.

¹H-NMR(CD₃OD) in ppm: δ 4.25 (m,1H), 4.15 (m,1H), 4.0 (m,1H),3.3–3.5 (m, 3H), 1.3 (d, 3H).

In a similar way the following compounds were prepared:
(3R,4R)-2-(1-Hydroxypentyl)-3,4-pyrrolidinediol (Compound 2) from (3R,4R)-1-benzyl-3,4-dibenzyloxy-2-(1-hydroxypentyl)pyrrolidine.

¹H-NMR(CD₃OD) in ppm: δ 4.25 (m,1H), 4.15 (m,1H), 3.8 (m,1H), 3.2–3.5 (m, 3H), 1.3–1.7 (m,6H), 0.95 (t, 3H);

(3R,4R)-2-(1-Hydroxytridecyl)-3,4-pyrrolidinediol (Compound 3) from (3R,4R)-1-benzyl-3,4-dibenzyloxy-2-(1-hydroxytridecyl)pyrrolidine.

¹H-NMR(CD₃OD) in ppm: δ 3.1–4.3 (m,6H), 1.2–1.7 (m,22H), 0.9 (t, 3H).

(2R,3R,4R)-2-((1R)-1-Hydroxyethyl)-3,4-pyrrolidinediol (Compound 4) from (2R,3R,4R)-1-benzyl-3,4-dibenzyloxy-2-((1R)-1-hydroxyethyl)pyrrolidine;

(2R,3R,4R)-2-((1S)-1-Hydroxyethyl)-3,4-pyrrolidinediol (Compound 5) from (2R,3R,4R)-1-benzyl-3,4-dibenzyloxy-2-((1S)-1-hydroxyethyl)pyrrolidine;

(2S,3R,4R)-2-((1R)-1-Hydroxyethyl)-3,4-pyrrolidinediol (Compound 6) from (2S,3R,4R)-1-benzyl-3,4-dibenzyloxy-2-((1R)-1-hydroxyethyl)pyrrolidine;

(2S,3R,4R)-2-((1S)-1-Hydroxyethyl)-3,4-pyrrolidinediol (Compound 7) from (2S,3R,4R)-1-benzyl-3,4-dibenzyloxy-2-((1S)-1-hydroxyethyl)pyrrolidine;

(3R,4R)-2-(1-Hydroxyphenylbutyl)-3,4-pyrrolidinediol (Compound 8) from (3R,4R)-1-benzyl-3,4-dibenzyloxy-2-(1-hydroxyphenylbutyl)pyrrolidine.

¹H-NMR(CD₃OD) in ppm: δ 7.1–7.5 (m,5H), 3.4–4.7 (m,6H), 2.5–2.7 (m,1H), 2.1–2.2 (m, 1H), 1.2–1.9 (m, 4H);

(3R,4R)-2-Acetyl-3,4-pyrrolidinediol (Compound 9) from (3R,4R)-2-acetyl-1-benzyl-3,4-dibenzyloxypyrrolidine.

¹H-NMR(CD₃OD) in ppm: δ 4.2–4.8 (m,2H), 3.3–3.7 (m, 3H), 2.4 (s, 3H);

(3R,4R)-2-(1-Hydroxypropyl)-3,4-pyrrolidinediol (Compound 10) from (3R,4R)-1-benzyl-3,4-dibenzyloxy-2-propionylpyrrolidine.

¹H-NMR(CD₃OD) in ppm: δ 4.2–4.3 (m,2H), 3.7–3.8 (m,1H), 3.2–3.5 (m, 3H), 1.3–1.7 (m, 2H), 0.9 (t,3H).

We claim:
1. An optical isomer of a pyrrolidine compound having the formula I

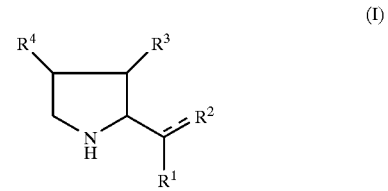

(I)

and pharmaceutically acceptable acid addition salts or hydrates or prodrugs thereof, wherein $R^1$ is straight or branched $C_{1-14}$-alkyl optionally substituted with $C_{3-7}$-cycloalkyl, $C_{1-6}$-alkoxy, phenoxy, perhalomethyl, halogen, optionally substituted phenyl;

C═══R² is optionally C═R² or C—R²

R2 is oxygen, hydroxy, halogen, amino or mercapto, $R^3$ and $R^4$ independently are hydroxy, halogen, amino or mercapto, wherein the optical isomer is (2R,3R,4R) or (2S,3S,4S).

2. A compound according to claim 1 wherein C═══R² is C—R2 wherein R2 has the meaning defined in claim 1.

3. A compound according to claim 2 wherein R2 is hydroxy.

4. A compound according claim 1 wherein R3 and R4 are hydroxy.

5. An optical isomer or mixture of optical isomers, according to claim 2 selected from the group consisting of:
(2R,3R,4R)-2-acetyl-3,4-pyrrolidinediol,
(2R,3R,4R)-2-(1-hydroxyethyl)-3,4-pyrrolidinediol,
(2R,3R,4R)-2-(1-hydroxypropyl)-3,4-pyrrolidinediol,
(2R,3R,4R)-2-(1-hydroxypentyl)-3,4-pyrrolidinediol,
(2R,3R,4R)-2-(1-hydroxytridecyl)-3,4-pyrrolidinediol,
(2S,3S,4S)-2-acetyl-3,4-pyrrolidinediol,
(2S,3S,4S)-2-(1-hydroxyethyl)-3,4-pyrrolidinediol,
(2S,3S,4S)-2-(1-hydroxypropyl)-3,4-pyrrolidinediol,
(2S,3S,4S)-2-(1-hydroxypentyl)-3,4-pyrrolidinediol,
(2S,3S,4S)-2-(1-hydroxytridecyl)-3,4-pyrrolidinediol,
(2R,3R,4R)-2-((1R)-1-hydroxyethyl)-3,4-pyrrolidinediol,
(2R,3R,4R)-2-(1R)-1-hydroxypropyl)-3,4-pyrrolidinediol,
(2R,3R,4R)-2-((1R)-1-hydroxypentyl)-3,4-pyrrolidinediol,
(2R,3R,4R)-2-((1R)-1-hydroxytridecyl)-3,4-pyrrolidinediol,
(2S,3S,4S)-2-((1R)-1-hydroxyethyl)-3,4-pyrrolidinediol,
(2S,3S,4S)-2-((1R)-1-hydroxypropyl)-3,4-pyrrolidinediol,
(2S,3S,4S)-2-((1R)-1-hydroxypentyl)-3,4-pyrrolidinediol,
(2S,3S,4S)-2-((1R)-1-hydroxytridecyl)-3,4-pyrrolidinediol,
(2R,3R,4R)-2-((1S)-1-hydroxyethyl)-3,4-pyrrolidinediol,
(2R,3R,4R)-2-((1S)-1-hydroxypropyl)-3,4-pyrrolidinediol,
(2R,3R,4R)-2-((1S)-1-hydroxypentyl)-3,4-pyrrolidinediol,
(2R,3R,4R)-2-((1S)-1-hydroxytridecyl)-3,4-pyrrolidinediol,
(2S,3S,4S)-2-((1S)-1-hydroxyethyl)-3,4-pyrrolidinediol,
(2S,3S,4S)-2-((1S)-1-hydroxypropyl)-3,4-pyrrolidinediol,
(2S,3S,4S)-2-((1S)-1-hydroxypentyl)-3,4-pyrrolidinediol, and
(2S,3S,4S)-2-((1S)-1-hydroxytridecyl)-3,4-pyrrolidinediol,
or a pharmaceutically acceptable salt or hydrate thereof.

6. A compound according to claim 1 which is active as an inhibitor of glucose production.

7. A compound according to claim 1 which is active as an inhibitor of glycogen phosphorylase enzymatic activity.

8. A pharmaceutical composition comprising a compound according to claim 1 or a pharmaceutical acceptable salt thereof, or any optical isomer or mixture of optical isomers, or any tautomeric form together with one or more pharmaceutically acceptable carriers or diluents.

9. The pharmaceutical composition according to claim 8 in the form of an oral dosage unit or parenteral dosage unit.

10. A pharmaceutical composition according to claim 8 wherein said compound is administered as a dose in a range from about 2 to 500 mg per day.

11. A method of treating or preventing diseases of the endocrinological system in a subject in need thereof comprising administering an effective amount of a compound according to any of the claims 1 to said subject.

* * * * *

UNITED STATES PATENT AND TRADEMARK OFFICE
CERTIFICATE OF CORRECTION

PATENT NO. : 5,952,363
DATED : September 14, 1999
INVENTOR(S) : Kristiansen, et al.

It is certified that error appears in the above-identified patent and that said Letters Patent is hereby corrected as shown below:

Col. 16, line 27, add new claim 12 as follows:

--12. A method of treating diabetes comprising administering to a subject in need thereof an effective amount of a compound of claim 1.--

Signed and Sealed this

Fourteenth Day of March, 2000

Attest:

Q. TODD DICKINSON

*Attesting Officer*     *Commissioner of Patents and Trademarks*